(12) United States Patent
Tunesi

(10) Patent No.: US 10,549,886 B2
(45) Date of Patent: Feb. 4, 2020

(54) LIGHT MEMBER ON A PACKAGE TO PROVIDE INFORMATION TO A USER

(71) Applicant: Boehringer Ingelheim Vetmedica GmbH, Ingelheim am Rhein (DE)

(72) Inventor: Cristiano Tunesi, Sant Cugat del Valles (ES)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 0 days.

(21) Appl. No.: 15/841,487

(22) Filed: Dec. 14, 2017

(65) Prior Publication Data

US 2018/0170618 A1    Jun. 21, 2018

Related U.S. Application Data

(60) Provisional application No. 62/435,096, filed on Dec. 16, 2016.

(51) Int. Cl.
*B65D 23/14* (2006.01)
*B65D 85/00* (2006.01)
(Continued)

(52) U.S. Cl.
CPC ............. *B65D 23/14* (2013.01); *B65D 85/70* (2013.01); *G08B 5/36* (2013.01); *G08B 21/182* (2013.01);
(Continued)

(58) Field of Classification Search
CPC .... A61J 1/18; A61J 7/00; A61J 7/0076; A61J 2205/20; A61J 2205/60; B65D 23/14;
(Continued)

(56) References Cited

U.S. PATENT DOCUMENTS 4,223,801 A * 9/1980 Carlson ................. A61J 7/0472
206/533
4,895,257 A * 1/1990 Winslow ................... A61F 9/08
116/205
(Continued)

FOREIGN PATENT DOCUMENTS

DE          43 16 688 A1   11/1994
DE   10 2016 001 923 A1    8/2017
(Continued)

*Primary Examiner* — Bryon P Gehman
(74) *Attorney, Agent, or Firm* — David S. Safran; Roberts Mlotkowski Safran Cole & Calderon, P.C.

(57) ABSTRACT

Packages that include at least one medicament therein include at least one light member affixed thereto that is capable of emitting light upon activation. The light member is activated upon the opening of the package such that, upon opening, the light member fluoresces or otherwise emits light to provide information to an end user. In some embodiments, the light generated by the light member allows the end user to locate the package in dark conditions. In other embodiments, the light generated by the light member may be configured to emit only for a time period equal to a viability time period of the medicament within the package or to change color at a time period equal to the viability time period of the medicament within the package to alert an end user that the medicament is no longer useable.

13 Claims, 14 Drawing Sheets

(51) Int. Cl.
*G08B 5/36* (2006.01)
*G08B 21/18* (2006.01)
*F21Y 115/10* (2016.01)
*F21K 2/06* (2006.01)
*F21V 23/04* (2006.01)
*H05B 37/02* (2006.01)

(52) U.S. Cl.
CPC ...... *B65D 2203/02* (2013.01); *B65D 2203/12* (2013.01); *F21K 2/06* (2013.01); *F21V 23/04* (2013.01); *F21Y 2115/10* (2016.08); *H05B 37/0281* (2013.01)

(58) Field of Classification Search
CPC ...... B65D 51/24; B65D 51/248; B65D 85/00; B65D 85/70; B65D 2203/02; B65D 2203/12; F21V 23/04; F21Y 2115/10; F21K 2/06; G08B 1/08; G08B 5/36; G08B 21/18; G08B 21/182; G08B 21/24; H05B 37/0281
USPC ........... 206/459.1, 459.5; 340/487.1, 815.45, 340/815.53
See application file for complete search history.

(56) References Cited

U.S. PATENT DOCUMENTS

| | | | | |
|---|---|---|---|---|
| 5,313,439 | A * | 5/1994 | Albeck | A61J 7/0409 116/308 |
| 5,838,224 | A * | 11/1998 | Andrews | A61J 7/0481 340/309.7 |
| 6,474,467 | B1 * | 11/2002 | Kurdian | B65D 23/00 206/219 |
| 6,826,119 | B2 * | 11/2004 | Fortune | G07F 9/02 235/462.01 |
| 7,392,953 | B2 * | 7/2008 | Chu | G06K 17/0022 235/492 |
| 7,643,378 | B2 * | 1/2010 | Genosar | B65D 33/2591 206/459.1 |
| 8,162,914 | B2 | 4/2012 | Kraushaar et al. | |
| 9,078,809 | B2 * | 7/2015 | Bochenko | A61J 1/2062 |
| 9,308,151 | B2 * | 4/2016 | Chaturvedi | A61J 1/10 |
| 9,311,452 | B2 * | 4/2016 | Dickie | A61J 1/03 |
| 9,474,692 | B2 | 10/2016 | Rauleder et al. | |
| 9,891,202 | B2 * | 2/2018 | Rolff | B65D 25/54 |
| 2002/0139708 | A1 * | 10/2002 | Lien | B65D 25/10 206/534 |
| 2006/0139928 | A1 * | 6/2006 | Griffiths | B65D 51/248 362/276 |
| 2008/0255515 | A1 | 10/2008 | Grinberg | |
| 2012/0323208 | A1 | 12/2012 | Bochenko et al. | |
| 2014/0251851 | A1 * | 9/2014 | Huntley | B65D 51/248 206/459.1 |
| 2015/0261192 | A1 * | 9/2015 | Spivack | G04G 19/06 206/459.1 |
| 2015/0332575 | A1 | 11/2015 | Huntley | |
| 2016/0166471 | A1 | 6/2016 | Tobescu | |
| 2016/0228328 | A1 | 8/2016 | Wengreen et al. | |
| 2016/0361231 | A1 | 12/2016 | Chou et al. | |

FOREIGN PATENT DOCUMENTS

| | | |
|---|---|---|
| WO | 2014/020326 A2 | 2/2014 |
| WO | 2015/075221 A1 | 5/2015 |

* cited by examiner

LIGHT MEMBER ON A PACKAGE TO PROVIDE INFORMATION TO A USER

BACKGROUND OF THE DISCLOSURE

Field of the Disclosure

The present disclosure generally relates to packages including one or more medicaments therein, such as a vaccine. In particular, the present disclosure relates to packages, such as medication bottles, that include one or more light members thereon that may be activated at a desired time to provide an end user of the package with information about the package or the contents therein. The packages including the light members thereon may reduce improper use of the medicament contained therein and improve overall compliance with instructions for proper use.

Description of Related Art

Farm animals receive numerous vaccines and medicaments over their lifetime to ensure their health and well-being. Some vaccinations are given once during the life of the animal while others are given annually. To save on costs, many farmers administer the vaccinations themselves rather than enlisting the services of a professional veterinarian. In some countries, health and safety regulations permit the farmer to administer the vaccinations to their herd, while in other countries a professional veterinarian is required.

Bovine viral diarrhea ("BVD") is the number one economically significant disease in cattle worldwide with infections occurring in all countries where cattle are raised. Although it is normally an infection of cattle, it has the ability to cause infections in other animals, such as pigs, sheep, goats, alpacas, deer, reindeer, and bison. An infection by this virus may be difficult to recognize and only a small percentage of infected animals show clinical signs of infection. This virus is well known for reducing milk production and increasing the risk of death. It can stress adult cattle and produce abortions and birth defects in calves that are born to mothers that are infected by the virus. The economic impact worldwide is substantial.

In spite of the availability of several commercial vaccines for BVD, infections are still quite common worldwide. Although conventional parenteral and intranasal BVD vaccines and methods of vaccination are available, they may not always be completely effective or safe. Also, cattle do not always respond uniformly immunologically to any vaccination. The range of immune responses can vary from no response at all to a very high level of response when such cattle are treated with the same batch of vaccines.

Vaccine failure is caused by many different factors, including the immune status of the animal, the environment in which the animal lives or the vaccine is administered, the specific pathogen, and improper administration. Eliminating or reducing the factors that contribute to vaccine failure is a significant issue for all farmers who manage herds because their economic livelihood depends on having healthy and productive animals. Because the farmer or professional veterinarian is often working in low light conditions, and are often interrupted when attempting to vaccinate their animals, one form of improper administration that occurs is administration of the vaccine after it is no longer viable. This can greatly reduce or entirely eliminate the effectiveness of the vaccine. Additionally, some vaccines have a short time period in which they remain viable once reconstituted or removed from refrigerated storage.

Furthermore, farmers often work with their animals in the early morning or under the poor lighting conditions of a barn. Farm animal vaccinations are often done in the winter when the animals are indoors which acerbates the low light conditions. In either case, the visibility of a vaccine bottle and/or the septa in the serum cap by which a syringe needle accesses the vaccine bottle contents is important. Poor visibility can lead to a need-stick or other adverse consequences for the farmer, veterinarian, or the animal.

Because it is impossible to determine if a vaccine or immunogenic composition is still viable after reconstitution or removal from refrigerated storage based on visual examination, a need exists to enable a farmer, veterinarian, or other end-user to make this determination in a simple, easy, and effective manner. Additionally, a need exists to assist the end-user in seeing and administering a vaccine to an animal under poor or low light conditions.

SUMMARY OF THE INVENTION

The present invention is generally directed to packages that include at least one medicament therein. The packages generally include at least one light member affixed thereto that is capable of emitting light upon activation. In many embodiments as described herein, the light member is activated upon the opening of the package such that upon opening, the light member fluoresces or otherwise emits light to provide information to an end user. In some embodiments, the light generated by the light member allows the end user to locate and utilize the package in dark conditions. In other embodiments, the light generated by the light member may be configured such that it is emitted only for a time period equal to the viability time period of the medicament contained within the package to alert an end user when the medicament is no longer useable. In still other embodiments, the light generated by the light member may be configured such that it changes color at a time period equal to the viability time period of the medicament contained within the package to alert an end user that the medicament is no longer useable.

The present invention is directed to a package comprising: (i) a medicament, and (ii) a light member. The light member is located on the exterior of the package, and is configured to provide information to an end user through the emission of light.

The present invention is further directed to a method for determining the viability of a medicament in a package. The method comprises (i) activating a light member on the package comprising said medicament when the package is opened; and (ii) observing the fluorescence in the light member.

The present invention is further directed to a method for determining the viability of a medicament in a package. The method comprises: (i) opening the package and activating a light member located on the package containing the medicament such that the light member emits fluorescent light; and (ii) observing a change in color in the light member over a period of time.

The features, aspects, and advantages of the present invention will become better understood when the following detailed description is read with reference to the accompanying drawings in which like characters represent like parts throughout the figures.

DETAILED DESCRIPTION OF THE INVENTION

Figure 1:
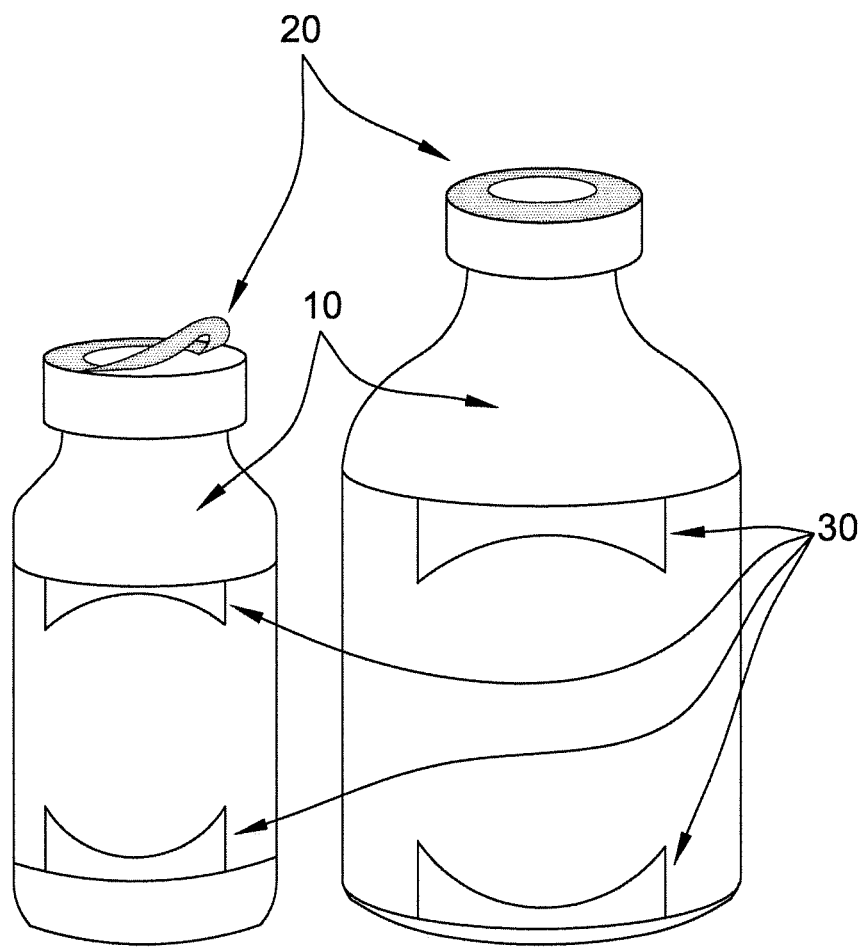
FIG. 1 shows an embodiment where the light member is on the serum cap of a package.

In the following specification and claims, reference will be made to a number of terms, which shall be defined to have the following meanings. The singular forms "a," "an," and "the" include plural references unless the context clearly dictates otherwise. The terms "comprising," "including," and "having" are intended to be inclusive and mean that there may be additional elements other than the listed elements. "Optional" or "optionally" means that the subsequently described event, structure, or circumstance may or may not occur, and that the description includes instances where the event, structure or circumstance occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

Various embodiments of the disclosure are discussed throughout this application. Any embodiment discussed with respect to one aspect of the disclosure applies to other aspects of the disclosure as well, and vice versa. Each embodiment described herein is understood to be embodiments of the disclosure that are applicable to all aspects of the disclosure. It is contemplated that any embodiment discussed herein can be implemented with respect to any method or composition of the disclosure, and vice versa.

Definitions

Unless defined herein and below in the remainder of the specification, all technical and scientific terms used herein have the same meaning as commonly understood by one of ordinary skill in the art to which the disclosure pertains.

The term "animal" as used herein refers to any animal which is the subject of a medical treatment for a medical condition unless stated otherwise. In some instances, the medical treatment may be prophylactic instead of reactive (e.g., a vaccine to prevent a medical condition rather than a medication to treat an already existing medical condition). It is understood that at least domestic animals, farm animals, zoo animals, sport animals and pet animals are within the scope of the meaning of the term. Desirably, the animal is a farm animal. Examples of farm animals include, but are not limited to, horses, cows, pigs, buffalo, bison, oxen, chickens, goats, sheep, donkeys, alpacas, llamas, rabbits, dogs, cats, ducks, and turkeys.

The terms "medicament", "medication", and "medicine" are used interchangeably herein and describe a pharmaceutical composition or product intended for the treatment or prevention of a medical condition having at least one symptom. The pharmaceutical composition or product will have a physiological effect on the animal when it is introduced into the body of an animal. The pharmaceutical composition or product can be in any suitable formulation unless a specific formulation type is required or disclosed.

"Immunologically protective amount" or "immunologically effective amount" or "effective amount to produce an immune response" of an antigen is an amount effective to induce an immunogenic response in the recipient. The immunogenic response may be sufficient for diagnostic purposes or other testing, or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity. "Immunogenic" means evoking an immune or antigenic response. Thus an immunogenic composition would be any composition that induces an immune response.

"Therapeutically effective amount" refers to an amount of an antigen or vaccine that would induce an immune response in a subject receiving the antigen or vaccine which is adequate in preventing or reducing the clinical signs or symptoms of disease, including adverse health effects or complications thereof, caused by infection with a pathogen, such as a virus or a bacterium. Humoral immunity or cell-mediated immunity or both humoral and cell-mediated immunity may be induced. The immunogenic response of an animal to a vaccine may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number, overall physical condition, and overall health and performance of the subject. The amount of a vaccine that is therapeutically effective may vary depending on the particular adjuvant used, the particular antigen used, or the condition of the subject, and can be determined by one skilled in the art.

An "immunogenic or immunological composition" and/or "vaccine" refers to a composition of matter that comprises at least one veterinary antigen and/or immunogenic portions thereof that elicit an immunological response in the host of a cellular or antibody-mediated immune response to the composition. In some desirable embodiments, an immunogenic composition induces an immune response and, more desirably, confers protective immunity against one or more of the clinical signs of at least one veterinary antigen.

The terms "vaccination" or "vaccinating" or variants thereof, as used herein means, but is not limited to, a process which includes the administration of a vaccine and/or an immunogenic composition that, when administered to an animal, elicits, or is able to elicit—directly or indirectly—, an immune response in the animal against at least one veterinary infectious disease.

As used herein, the term "viable" or any variants thereof, when used in reference to a medicament means that the medicament when administered to a patient in need thereof produce an immune response in said patient. It does not require that the immune response be the maximum possible or therapeutically effective. Both humoral and cell-mediated immune response are covered, and a viable medicament may produce either a humoral immune response, a cell-mediated immune response or both. If the medicament is a vaccine or immunogenic composition, the immune response may be partial or complete protection from the medical condition, and the protection may be permanent or temporary.

The light member as discussed further herein may use both fluorescence and/or chemiluminescence. Both result from the decay of a molecule in a higher energy or excited state back down to the ground state. This decay results in the release of energy and the emission of a photon; however, they are caused by different phenomenon. Fluorescence results from electronic excitation—a consequence of the molecule absorbing a photon initially. That is, a photon of light is absorbed and re-emitted. The same color may or may not be re-emitted as the molecule can lose energy, while in the excited state, through vibrational deactivation.

Chemiluminescence is caused by a molecular reaction of two (or more) ground state molecules producing a final molecule in an excited state. The energy in the reactants is translated into the products and, while forming the products, it also excites them. This excitation may lead to chemiluminescence. Some reactions also result in the formation of molecules in an excited state that result in the emission of a photon of light.

As a non-limiting example of chemiluminescence, Glow Sticks® emit a variety of colors based on the combination of three different chemicals: diphenyl oxalate, hydrogen peroxide and a fluorescent dye according to the following reaction:

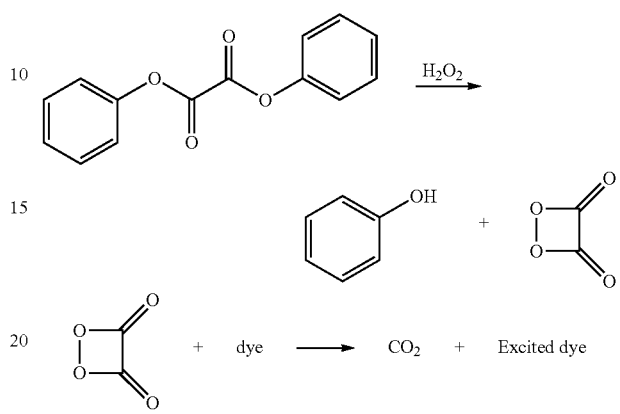

The selection of the fluorescent dye determines the color of the excited dye which is the source of the light emission observed by the end-user. Non-limiting examples of fluorescent dyes are rhodamine B (red), 5,12-bis(phenylethynyl)-naphthacene (orange), rubrene (yellow), 9,10-bis(phenylethynyl)anthracene (green), and 9,10-diphenylanthracene (blue). In the initial structural arrangement, the hydrogen peroxide is physically separated from the diphenyl oxalate and dye. Upon the application of force to the Glow Stick (i.e., bending it which ruptures the separator), the diphenyl oxalate and dye mix with the hydrogen peroxide thereby initiating a cascade which ultimately leads to the excitation of the dye, thereby causing the emission of light. Other chemiluminescent reactions are known in the art and any that emit light as required in the embodiments disclosed herein are acceptable.

Alternatively, the light source of the light member may be generated by a light emitting diode (LED). An LED is a semiconductor device that emits visible light, usually monochromatic, when an electric current passes through it. In such a configuration, the light member comprising the LED would have an actuation switch that includes at least two different actuation settings such that the LED could be turned on and off. In some embodiments, the light member using an LED would be removable from the package and transferable to another package. In some other embodiments, the light member using an LED would be single use and disposed after use.

In another embodiment, the emission of light is actuated by removal of a separator that prevents two or more chemical from mixing. Upon removal, the chemicals mix thereby causing a chemical reaction that emits light.

The color of the light emitted from the light member is not limited and may be selected from any color visible to the human eye. Examples include, but are not limited to, white, red, orange, yellow, green, blue, indigo and violet. Different shades and intensities are also not limited. In some embodiments, the color is desirably yellow or white. They are selected based on the desired characteristics of the light member. Additionally, more than one color may be emitted from a light member over time.

In another embodiment, the light emitted by a chemical reaction may be one color, but the packaging structure or exterior containment comprising the chemicals may be a different color thereby exhibiting a different color to the end-user. As a non-limiting example, a chemiluminescent reaction that emits white light can be encased in a plastic structure where the exterior of that plastic structure is green. The end user would see a green light rather than a white one. The color of the structure that encases the chemicals is not limited and may be selected as desired by the manufacturer of the package. As one non-limiting example, some manufactures have trademarks that comprise a specific color or combination of colors. The color of the encasement of the chemicals could be matched to that color or combination of colors thereby enhancing brand recognition.

Regardless of the source of the light, fluorescence, chemiluminescence or an LED, they are observationally identical—visible light is emitted that is observed by an end-user. Additionally, because fluorescence and chemiluminescence are so similar in their source and often confused for one another, these two terms are used interchangeably. The embodiments disclosed herein are related to the outwardly observed visual effect rather than the cause of that effect.

The packages and methods disclosed herein overcome the limitations present in presently available packages including medicaments and meet one or both of the unmet needs disclosed herein; that is, the packages and methods disclosed herein address either the need to provide the end-user with information regarding the viability of the medicament being administered to the animal or to assist the farmer with the visibility of a package under low light conditions. In some embodiments, the packages and methods disclosed herein overcome both unmet needs simultaneously.

A large variety of packaging types are known for use in medicinal applications and products. Examples of known packages include, but are not limited to, bottles, boxes, vacuum packs, and bags. The embodiments disclosed herein are suitable when applied to any type of package. Desirably, the package is for medicinal products or a medicament, and is a bottle. In another embodiment, the package is desirably a box in which the medicament is stored, shipped, or otherwise packaged prior to delivery to the end-user. In one non-limiting example, the package is a box that contains multiple bottles of a medicament that are delivered to a farmer or veterinarian. The multiple bottles of medicament inside the box may or may not have an individual light member for each individual bottle.

Some packaging for use with a medicament that requires regulatory approval will also be subject to regulatory requirements as determined under appropriate national authority, for example, by the United States Food and Drug Association. The light member disclosed herein, when integrated into to the label or exterior adornment of a package, will meet any required regulatory requirements if necessary. In some embodiments, there are no regulatory requirements that would apply to the light member. In other embodiments, there are regulatory requirements that apply to the light member.

In some embodiments, the package comprises a medicament, and the package comprises a light member that is configured to provide information to the end-user. The light member may be attached to the package when activated to produce light; or the light member may be activated to produce light and then subsequently attached to the package. In other embodiments, the light member may be activated to produce light and simply placed next to the package. The end-user may be a farmer, farm worker, veterinarian, veterinarian technician, or any individual who is providing medical treatment for an animal. In some desirable embodiments, the package is a bottle comprising an animal vaccine. In some embodiments, the bottle comprising the animal vaccine is suitably shaped and size for use with an animal vaccination gun. In some other embodiments, the information provided to the end-user is simply the location of the package or a specific part of the package under low light conditions. In some aspects, the information provided to the end-user is about the viability of the medicament inside the package. In some other aspects, the information provided is both regarding the viability of the medicament inside the package and the location of the package or specific part of the package under low light conditions.

Figure 11:
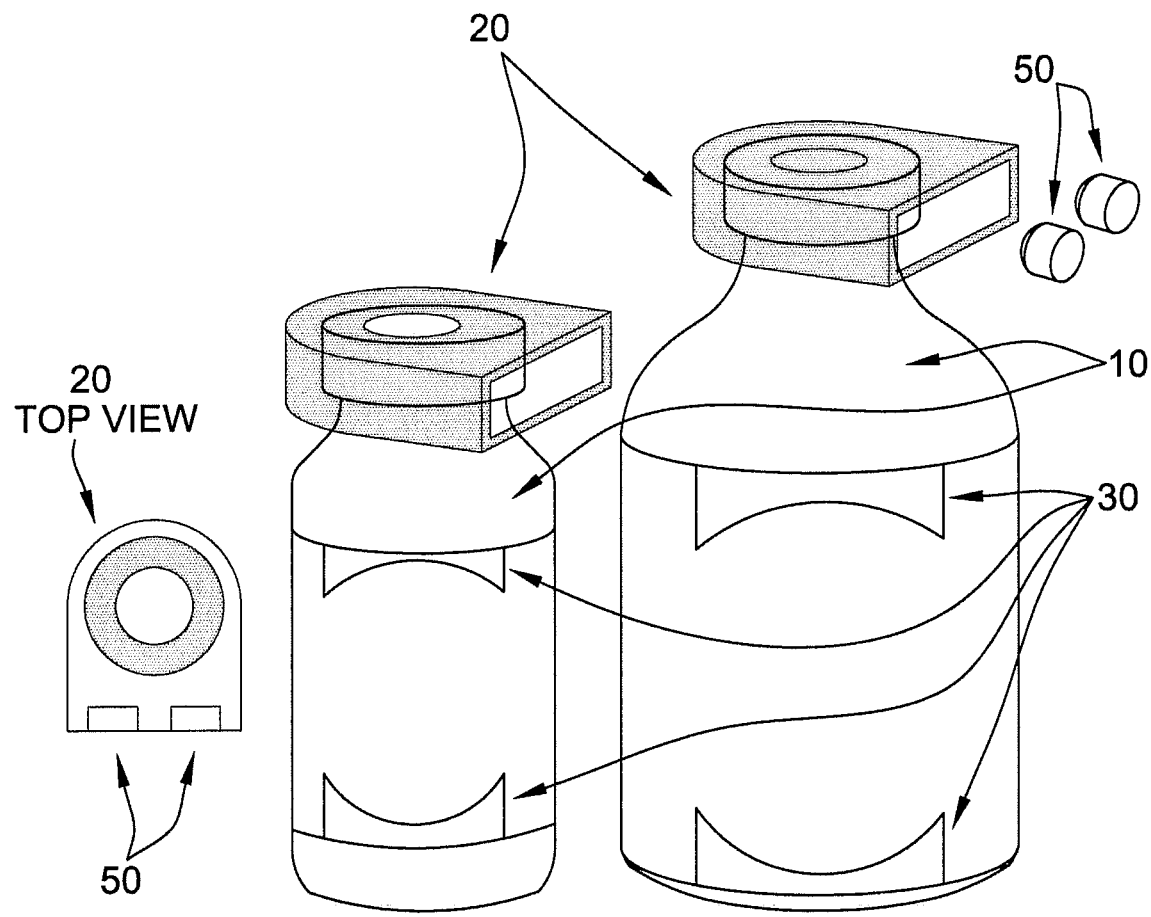
FIG. 11 shows an embodiment where the light member is a cap that fits over the serum cap of a package and includes an LED light source.

In yet another aspect, the light member is part of a kit. The kit comprises at least one package comprising a medicament and at least one light member. The medicament and the light member can be any embodiment disclosed elsewhere herein. As one nonlimiting example, the kit comprises two different vaccines for two different medical conditions. Included in said kit are two different colored light members. One white LED light member as described in FIG. 11 is included to enhance the visibility of the septa on the serum cap, and each vaccine comprises a light member as described in FIG. 8 already attached to the bottle wherein one vaccine has a green light member and the other vaccine has a yellow light member. Informational material in the form of written instructions may be included in the kit. Said written instructions may include any relevant information in relation to the kit, including, but not limited to, the manner in which to actuate the light members and instructions relating the length of time that the light member remains visible to the viability of the medicament.

Figure 7:
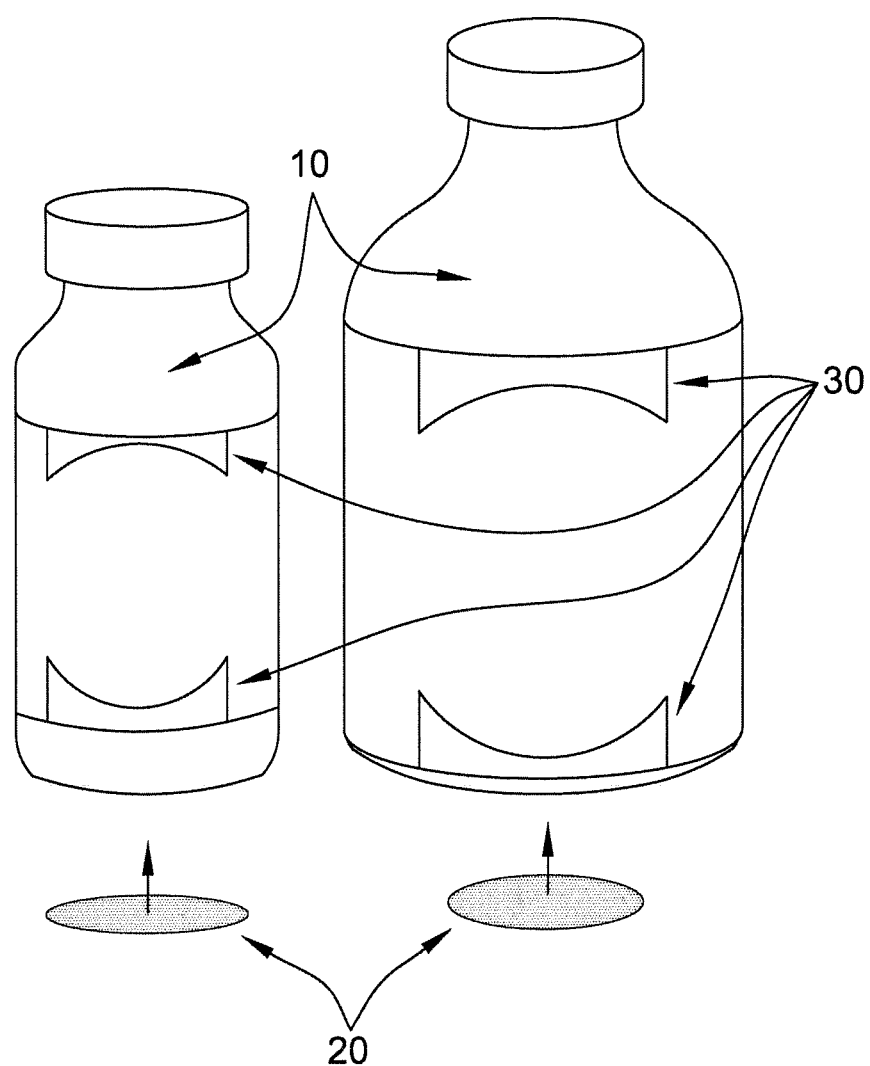
FIG. 7 shows an embodiment where the light member is attached to the bottom of a package.

As another nonlimiting example, the kit comprises a box with a fluorescent label; inside the box there is at least one bottle comprising a vaccine and at least one light member as illustrated in FIG. 7. The light member has a "peel and stick" adhesive that can be used to attach the light member to the bottom of the vaccine bottle. The light member is activated by pinching it forcefully enough to rupture the internal separator for the chemicals inside once the vaccine is either reconstituted or removed from refrigerated storage. Activation may be either prior to attaching to the bottle or any time thereafter as desired by the end-user.

The medicament in the package is not limited and may be any medicinal product. In some embodiments, the medical product has a limited viability when it is either reconstituted or removed from refrigerated storage. In some other embodiments, the medicament is a veterinary product selected from the group consisting of immunogenic compositions, antibiotics, vaccines, nutritional supplements, growth supplements, antifungal medication, antiparasitic medication, hormones and combinations thereof. In many embodiments, the medicament is a vaccine such as, for example a vaccine for BVD including Bovela®.

In many embodiments described herein, the signal to the end-user is in the form of emitted light. The light source may be fluorescence, chemiluminescence or a light emitting diode, and may be active or passive in nature. The light source is a light member that emits light upon actuation and is either integrated into external adornment of the package or is able to be attached to the exterior of the package by any suitable method, as noted above.

In some embodiments, the fluorescence is passive illumination. In such an aspect, the light member may be either combined with or separate from the label on the package. The light member may be fully or partially incorporated into the label of the package. In another aspect, the light member may be a separate structure that is attached to the package by the end-user at a designated time in a designated manner. In another aspect, the light member may be attached to the package prior to delivery to the end-user. For a passively light member, the fluorescence is activated by placing the light member under a light source for a predetermined period of time. Such light source may be artificial (e.g., a light bulb) or natural (e.g., the sun).

In some embodiments, the fluorescence is active illumination. In such an aspect, the light member may be either combined with or separate from the label on the package. The light member may be fully incorporated into the label of the package. In another aspect, the light member may be a separate structure that is attached to the package by the end-user as a designated time in a designated manner. In another aspect, the light member may be attached to the package prior to delivery to the end-user. For an actively light member, in some aspects, the fluorescence is activated by the mixing of two or more precursor chemicals. Such arrangements are known in the art. For example, a separator inside the light member can keep the precursor chemicals separate. Upon rupture of the separator, the precursor chemicals mix resulting in a fluorescent reaction. Rupture can be caused by exerting force on the separator in the form of shaking, compression or bending. As a non-limiting example, the light member can be compressed by the end user thereby causing the rupture of the separator which permits mixing of the precursor chemicals. In another aspect, when the light member comprises an LED, actuation is done using an actuation switch on the LED that comprises at least two settings—on and off. As non-limiting examples, actuation of the LED can be by a mechanical action such as twisting, turning, or compression of the actuation switch.

In some embodiments, the light member is not affixed to the package prior to delivery to the end user. Either subsequent to, coincident with or shortly after actuation of the light member, the light member can be attached to the package. In another aspect, the light member is activated, but the light member is not attached to the package. Attachment may be permanent or temporary. If the attachment is temporary, removal of the light member can be done such that the light member is preserved for use on another package. Methods of attachment are not limited and may include an adhesive (e.g., glue), tape, and the like. In some embodiments, attachment of the light member involves inserting the package into a sleeve or band that comprises the light member. Methods of attachment are known in the art, and any method of attachment that does not interfere with the light emitted by the light member or the contents of the package is acceptable. In some embodiments, the attachment is via a "peel and stick" method, whereby a protective cover is removed from an adhesive on one part of the light member, and the exposed adhesive is pressed against the package in any suitable location. In another non-limiting example, the light member has a dry glue on part of one surface that is moistened to render the glue sticky. As another example, the light member (described in FIGS. 4 and 5 below) in the form of a sleeve can be slid on and off of the package and readily placed on another package. In another embodiment, the light member is in the form of a fluorescent paint that is coated onto the package prior to delivery or sale to the end-user. The fluorescent paint would not affect the contents of the package or pose health and safety risks to the animals or the end-user.

Fluorescence and chemiluminescence are known to be transient processes that last for a limited period of time. They have a finite lifetime that can be controlled based on careful selection of the materials and chemicals involved. In some aspects, the time period that the fluorescence lasts from 1 to 100 hours and all integral values in between, specifically including 1 hour, 2 hours, 3 hours, 4 hours, 5 hours, 6 hours, 7 hours, 8 hours, 9 hours, and 10 hours. In some embodiments the fluorescence is tailored to last for a predetermined period of time that is matched to some property of the medicament inside the package. In one desirable embodiment, the property of the medicament is the length of time it remains viable after reconstitution or removal from refrigerated storage. In some embodiments, the light members emit light for 1 hour, 2 hours, 3 hours, 4 hours, 5 hours, 6 hours, 7 hours, 8 hours, 9 hours, 10 hours, 11 hour, 12 hours, 13 hours, 14 hours, 15 hours, 16 hours, 17 hours, 18 hours, 19 hours, 20 hours, 25 hours, 30 hours, 35 hours, 40 hours, 45 hours, 50 hours, 55 hours, 60 hours, 65 hours, 70 hours, 80 hours, 90 hours, or 100 hours after actuation.

It is known that some medicaments have limited viability after reconstitution or removal from refrigerated storage. In some embodiments, the length of time that the light member emits light is matched as closely as possible to the time period that the medicament remains viable. As a non-limiting example, some animal vaccines are viable for 8 hours after reconstitution or removal from refrigerated storage. As such, the time period that the light member continues to emit light would be 8 hours. When light is no longer emitted from the light member, the end-user would know that the medicament was no longer viable and should not be used. It is understood that the time period that a medicament remains viable after reconstitution or removal from refrigerated storage may vary depending on the environmental conditions the medicament is kept and/or the manner in which it is used. The time period that the light member continues to emit light would be determined based on the instructions included with the medicament.

In some embodiments two or more light members are used simultaneously for one package. Each light member may be the same or different. Each light member may have a different color or time period for which light is visible. For example, two different colors with two different time periods may be used to provide different information to the end-user. The color of the light member is not limited and may be any color visible to the human eye. Examples include, but are not limited to, white, red, orange, yellow, green, blue, indigo and violet. Different shades and intensities are also not limited. They are selected based on the desired characteristics of the light member. Additionally, one or more light member may be used that changes color after a specific time period to provide information to the end user (such as that the medicament is no longer viable, etc.)

Figure 8:
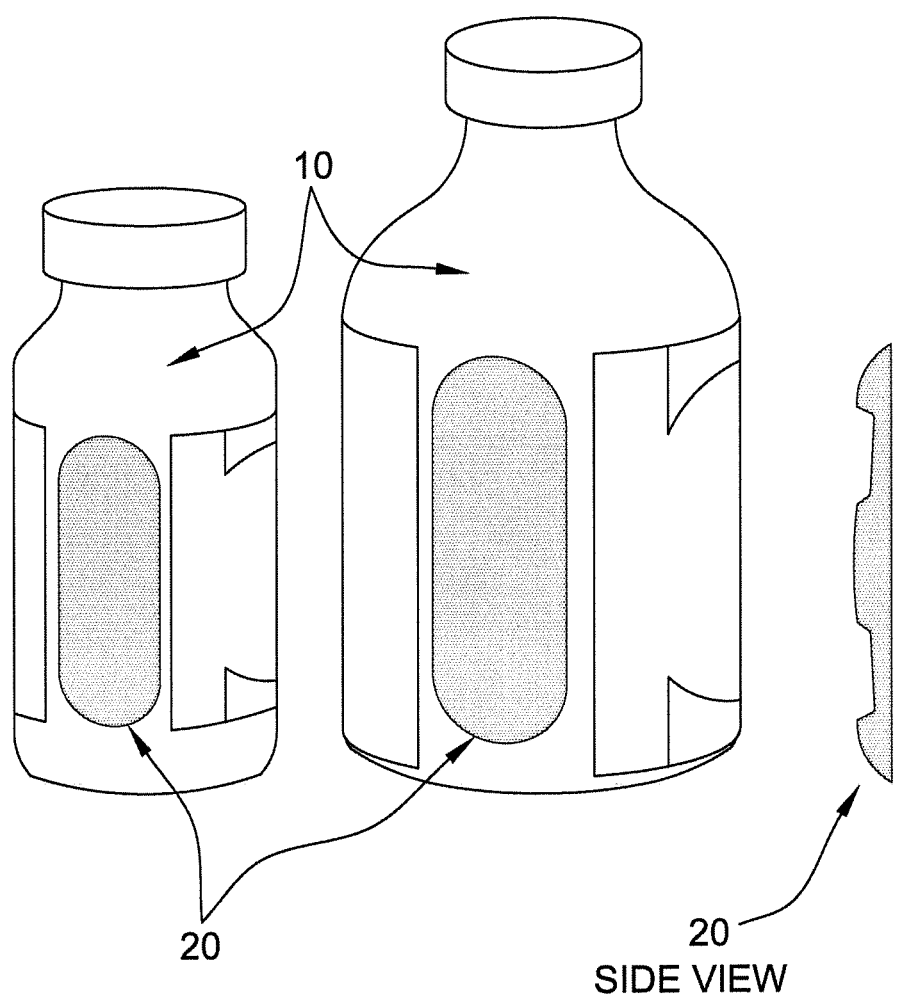
FIG. 8 shows an embodiment where the light member is attached to the side of a package.

In one non-limiting example, a red light member on the serum cap of a bottle (as shown in FIG. 1 discussed below) is used to assist the end-user in properly locating the septa for syringe access to the medicament while a second green light member is attached to the side of the package (as shown in FIG. 8 discussed below) to indicate the viability of the medicament inside the package. In embodiments with more than one light member, each light member may individually be active or passively illuminated, and may individually be integrated into the package or attached to the external adornment of package. Each light member may be the same or different in color. Each light member may use a different source of light.

In another non-limiting example, a light member using an LED light source (as shown in FIG. 11 discussed below) is attached to the serum cap of the package to assist the end-user in locating the septa under low light conditions while an active chemiluminescent light member having a lighted time period of 8 hours (as shown in either FIG. 7 or 8 discussed below) is activated upon reconstitution of a medicament that is known to have 8 hours of viability after reconstitution. After the 8-hour time period elapsed and the chemiluminescent light member is no longer visible, any remaining medicament would be discarded. The LED light member would be removed, deactivated, and either placed on a new bottle of medicament or saved for future use.

In another non-limiting example, the label of a package for a first medicament comprising a green light member and the label of a different package for a second medicament comprising a red light member are used simultaneously under low or poor lighting conditions. The color difference would allow identification of each medicament where one group of animals is given the first medicament and a second, different group of animals, is given the second medicament. Such color differentiation could be combined with a different color marking directly on the animal, for example, a non-toxic paint or dye, to help determine which animals have been given which medicament.

Also disclosed herein is a method for determining the viability of a medicament in a package. The method comprises actuating the light member as described elsewhere herein when the package comprising the medicament is initially opened or brought into use and observing the loss of fluorescence after a predetermined period of time. The complete loss of fluorescence indicates that the medicament is no longer viable. In some embodiments, the light member is attached to the package prior to actuation. In some embodiments, the light member is activated and then attached to the package by the end-user.

A package comprising a medicament and the light member is considered to be opened or brought into use when the end-user prepares to administer the medicament to an animal or animals. In some embodiments, the package is removed from refrigerated storage and allowed to warm to ambient temperature. Refrigerated storage does not suggest or require any specific temperature, only that the temperature be below standard ambient temperature, usually 25° C., in order to preserve the medicament for an extended period of time prior to use. Some forms of refrigerated storage are below the freezing point of the medicament, including below 0° C. In some embodiments, opening or bringing into use means that a solid is reconstituted with a liquid such that the resulting solution can be administered to an animal via syringe, vaccination gun, or similar method. Other means of opening and bringing into use are known and will be specific to the medicament and the steps necessary before it can be administered to an animal or animals. This is non-limiting and illustrated herein only by way of example. Other means as are known in the art are also encompassed herein.

Activation of the light member can be by causing two or more precursor chemicals to mix inside the light member. For example, a separator inside the light member can keep the precursor chemicals separate. Upon rupture of the separator the precursor chemicals mix resulting in a fluorescent reaction. Rupture can be caused by exerting force on the separator in the form of compression or bending. As a non-limiting example, the light member can be compressed or bent by the end user thereby causing the separator to rupture which causes mixing of the precursor chemicals.

In some other embodiments, actuation of the light member is done by exposing the light member to light for a set time period. The light may be may be man-made (e.g., a lightbulb) or natural (e.g., sunlight). The set time period to activate the light member will vary depending on the nature of the light member and the length of time the end-user desires the fluorescence to continue. Instructions for actuation for these embodiments, including the set time period required for actuation, would be included with the package and the light member.

The Figures included herein illustrate one desirable embodiment of the package that comprises a light member—a bottle with a serum cap and septa that is commonly used for animal vaccines and other medicaments. This is not intended to be limiting and other types of packages are included in any and all embodiments disclosed elsewhere herein.

As shown in FIG. 1, light member 20 is integrated into the septum cap of package 10 having label 30 comprising a medicament (not shown). It may be in the form of a ring that partially (not-shown in the Figure) or completely (as shown in the Figure) outlines the mouth of package 10. In such an embodiment, the outline around the mouth of the package does not interfere with access to the contents of the package. Additionally, the light member may be permanently affixed to the serum cap or it may be added by the end-user. The light member would not interfere with the needle in accessing the contents of the package. Such a light member may be in the form of an outline of the septum cap thereby providing an non-illuminated target for the syringe needle as shown. In another aspect, the septa of the serum cap itself would be fluorescent (not shown in the Figure), thereby providing an illuminated target for the syringe needle. In still yet another aspect, the light member is in the form of a fluorescent paint that is painted onto the package. As one non-limiting example, the fluorescent paint encircles the septa of the serum cap in the same manner as illustrated in FIG. 1. The paint would be applied by the manufacturer at the point of origin or prior to delivery to the end-user and be permanently affixed to the serum cap. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

Figure 2:
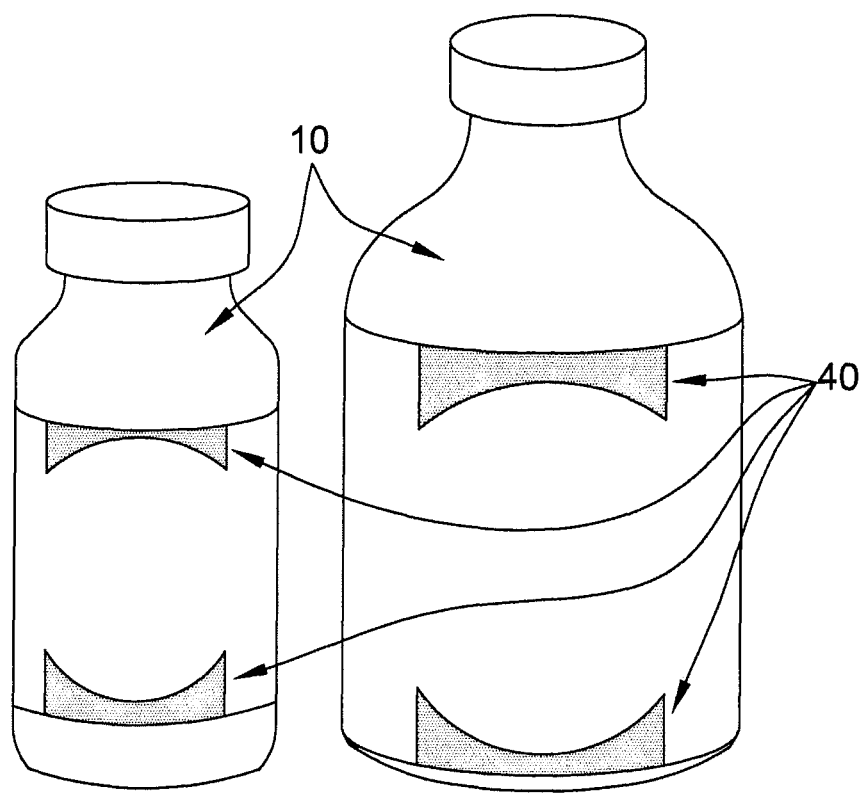
FIG. 2 shows an embodiment where the light member is integrated into the label of a package.

As shown in FIG. 2, the package 10 comprises the light member 40 that is completely integrated into the label of the package. Different parts of the label may comprise the light member, and the example shown here is only illustrative, not limiting. In some embodiments, the light member comprises only part of the label. In some embodiments, the light member comprises the entire label. In this example, the fluorescence does not interfere with the contents of the label leaving it clearly legible to the end-user as required under regulatory guidelines. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

Figure 3:
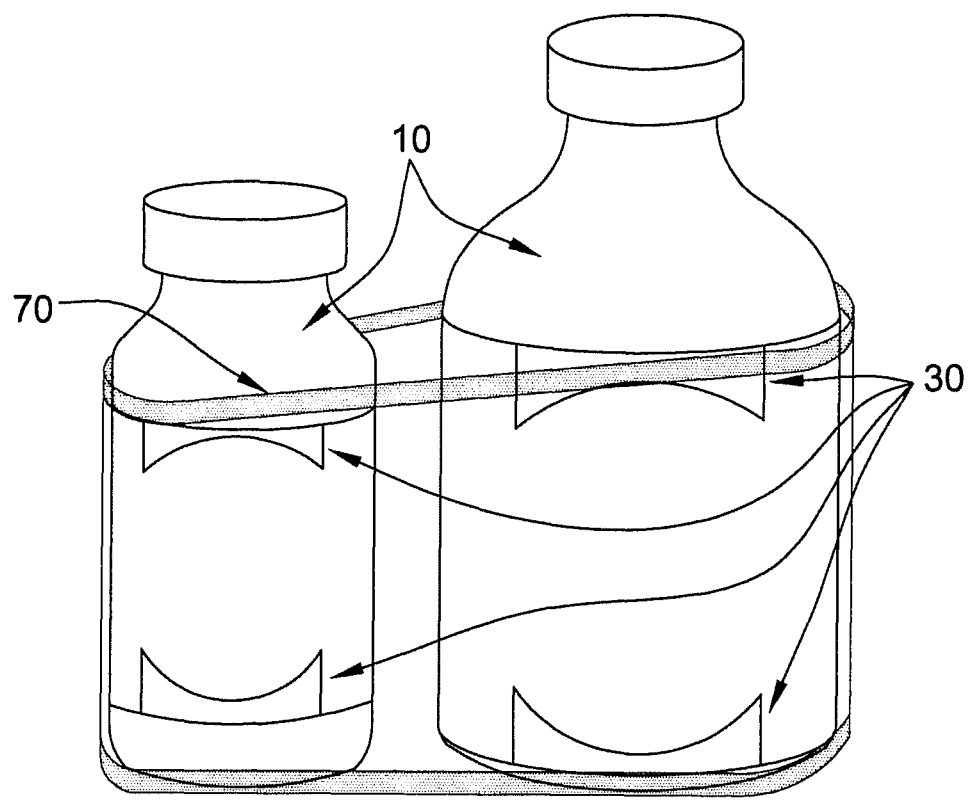
FIG. 3 shows an embodiment where the light member is a sleeve that fits around two separate packages that contain a medicament.

As shown in FIG. 3, the package 10 comprises the light member 70 that is integrated into the external packaging of a two-part medicament. Some medicaments, including animal vaccines, are commercially available as a lyophilized solid that must be reconstituted prior to administration to the animal. Different parts of the label on the packaging comprising both components of the medicament may comprise the light member, and the example shown here is only illustrative, not limiting. In this example, the fluorescence does not interfere with the contents of the label leaving it clearly legible to the end-user as required under regulatory guidelines. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

Figure 4:
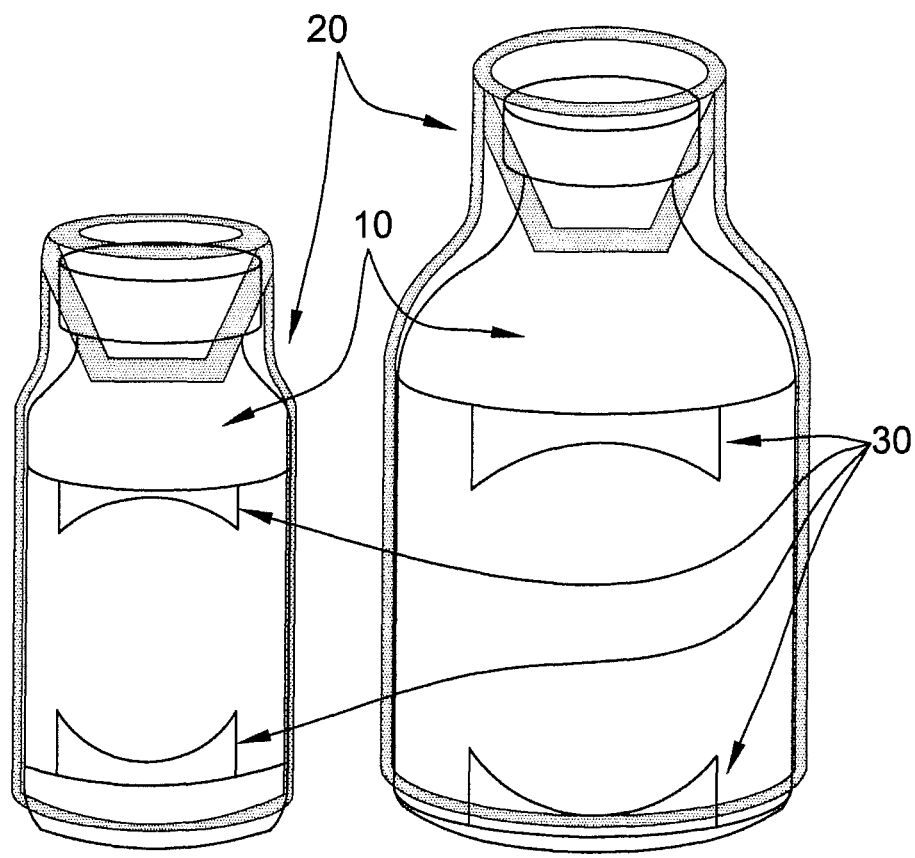
FIG. 4 shows an embodiment where the light member is a sleeve that fits over a package.
Figure 5:
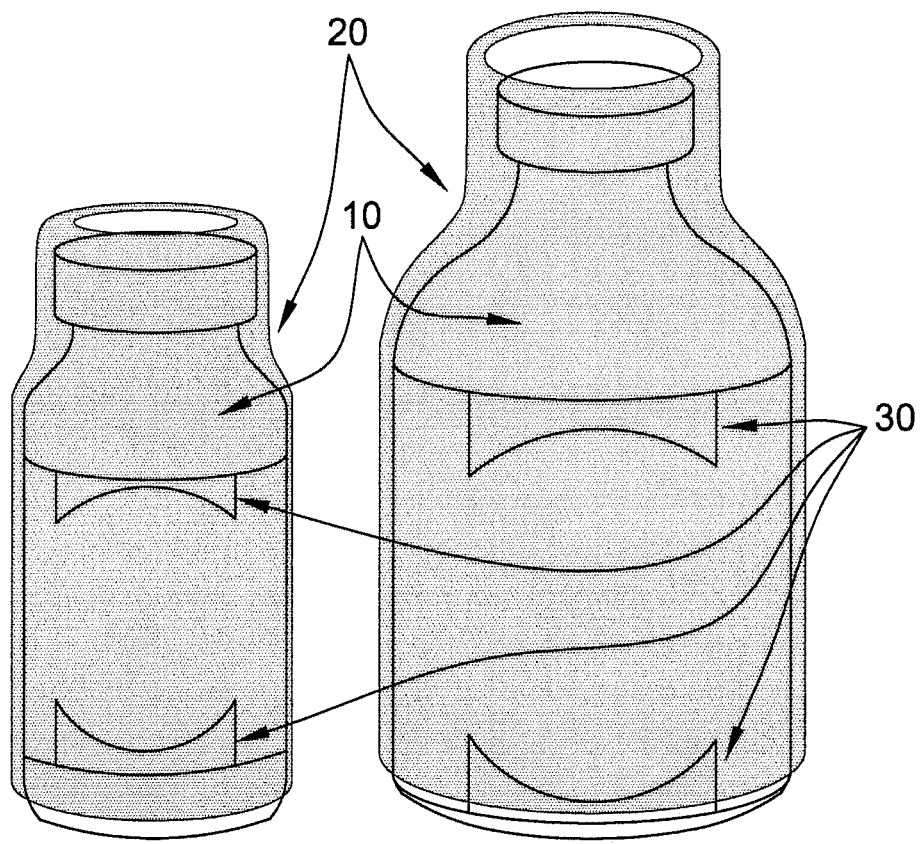
FIG. 5 shows another embodiment where the light member is a sleeve that fits over a package.

As shown in FIGS. 4 and 5, the light member 20 is in the form of a sleeve that is placed around the package 10 comprising a medicament. The sleeve may be placed around the package before or after actuation of the light member. Additionally, the sleeve may be in place prior to delivery to the end user, or it may be put in place by the end user. In FIG. 4, the sleeve is mostly transparent except for the fluorescent outline provided by the sleeve and the label 30 is visible through the sleeve. Label information may or may not be provided on the sleeve thereby improving identification and brand recognition under poor light conditions. Such a configuration would be useful under circumstances where two or more different medicaments must be administered at the same time. In FIG. 5, the entire sleeve surrounding the package 10 comprises the light member 20 and is fluorescent thereby improving visibility under poor light conditions. In all aspects, the light member would not interfere with or affect the medicament inside the package during access by a syringe needle. With this embodiment, the label 30 would not be visible through the sleeve. In some aspects, the package would be suitable for use with an animal vaccination gun, and the light member would not interfere with loading the package into the vaccination gun. The light member may use any source of lighting as disclosed herein.

Figure 6:
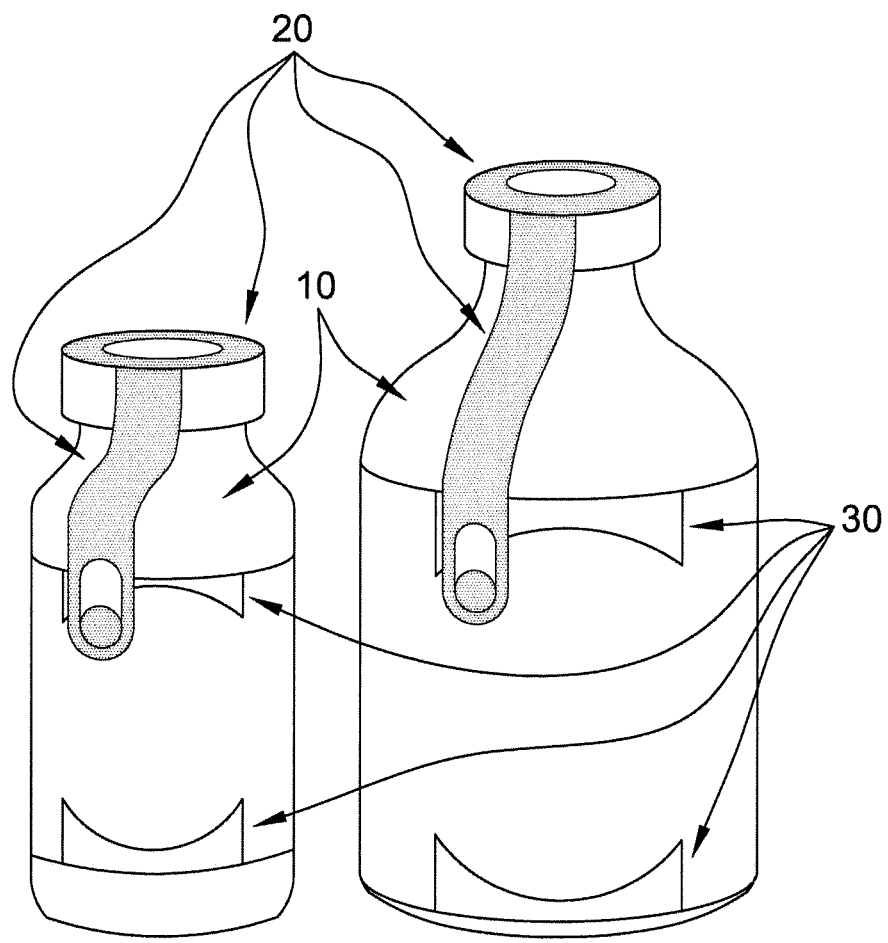
FIG. 6 shows an embodiment where the light member is attached to the serum cap of a package.

As shown in FIG. 6, the light member 20 is in the form of a structure that is attached to the serum cap of the package 10 comprising a medicament. In such an embodiment, the outline around the mouth of the package does not interfere with access to the contents of the package or view of the label 30. Additionally, the light member may be permanently affixed to the serum cap or it may be added by the end-user. The light member would not interfere with the needle in accessing the contents of the package. Such a light member may be in the form of an outline of the septum cap thereby providing a non-illuminated target for the syringe needle similar to that illustrated in FIG. 1. Additionally, the part of the light member not encompassing the serum cap may or may not be attached to the side of the package. In some embodiments, the light member is completely attached to the package, while in other aspects, only the part of the light member surrounding the serum cap is attached. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

As shown in FIGS. 7 and 8, the light member 20 is in the form of a structure attached to the side (FIG. 8) or the bottom (FIG. 7) of the package 10. The light member may be attached to the package prior to delivery to the end-user or it may be attached by the end-user after delivery. In either aspect, the light member does not impede the label 30. A side view of the fluorescent member in FIG. 8 is also shown. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

Figure 9:
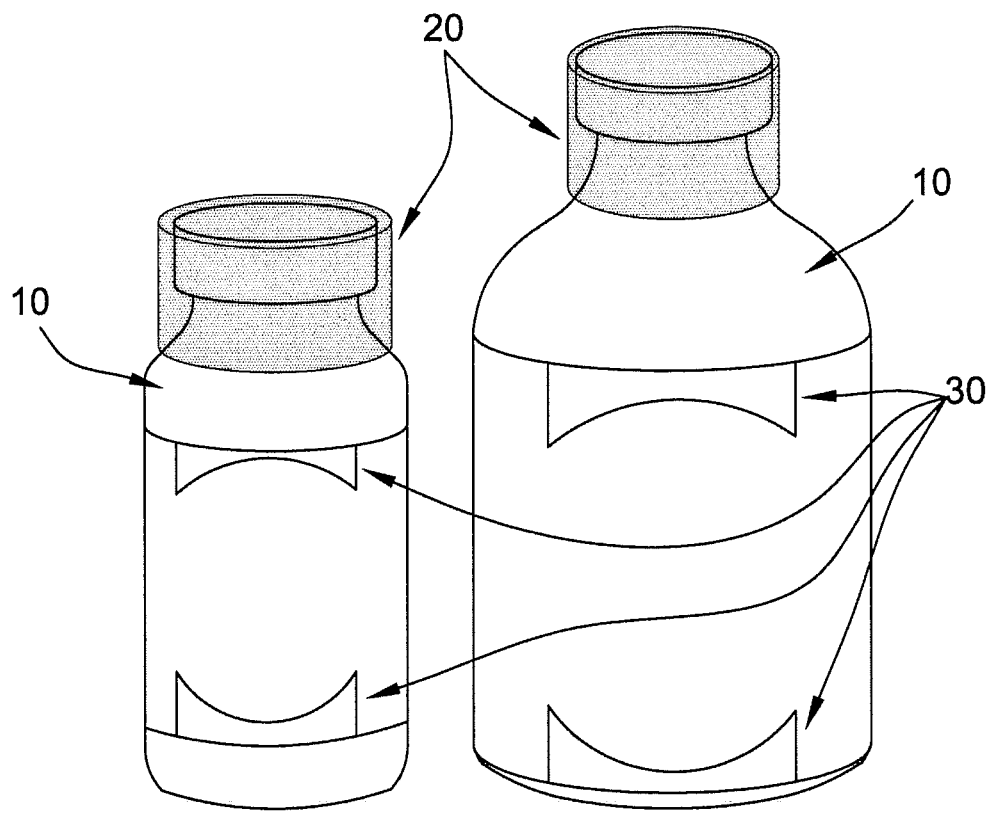
FIG. 9 shows an embodiment where the light member is a sleeve that fits around a serum cap on a package.

As shown in FIG. 9, the light member 20 comprises a sleeve or ring around the opening of the package 10. Such a ring can be put in place prior to delivery to the end user or by the end-user after delivery. This ring would provide improved illumination of the septum cap of the package thereby reducing the likelihood of sticking a syringe needle in the wrong location (e.g., the hand of the end-user holding the package). In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

Figure 10:
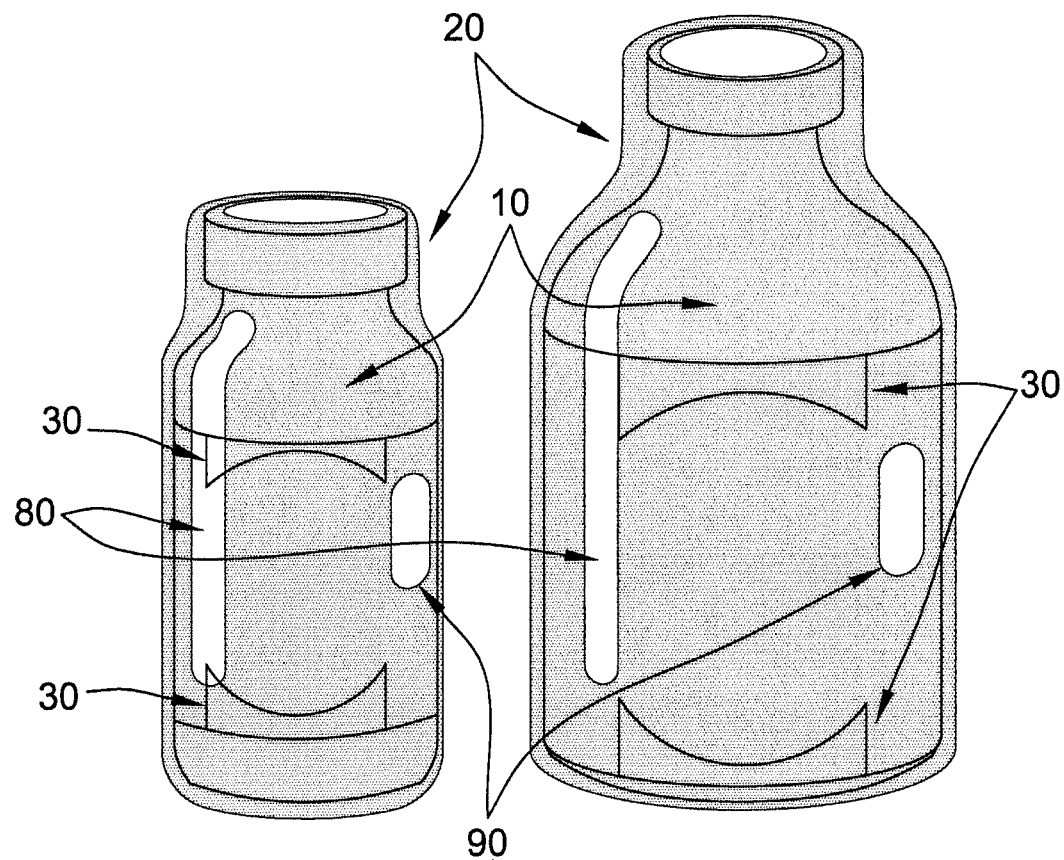
FIG. 10 shows an embodiment where the light member is a sleeve that fits over a package and includes an LED light source.

As shown in FIG. 10, the light member 20 comprises a sleeve that contains an additional opening 80 along the surface of the light member so that the end-user may more clearly observe the contents of the package 10. For example, the end-user may observe the amount of the medicament remaining inside the package. The light member may include a plurality of additional openings placed in any location on the light member. Additionally, as shown in this embodiment, the light member uses LED lighting and includes an on/off switch 90 for actuation on the side of the light member. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

Figure 12:
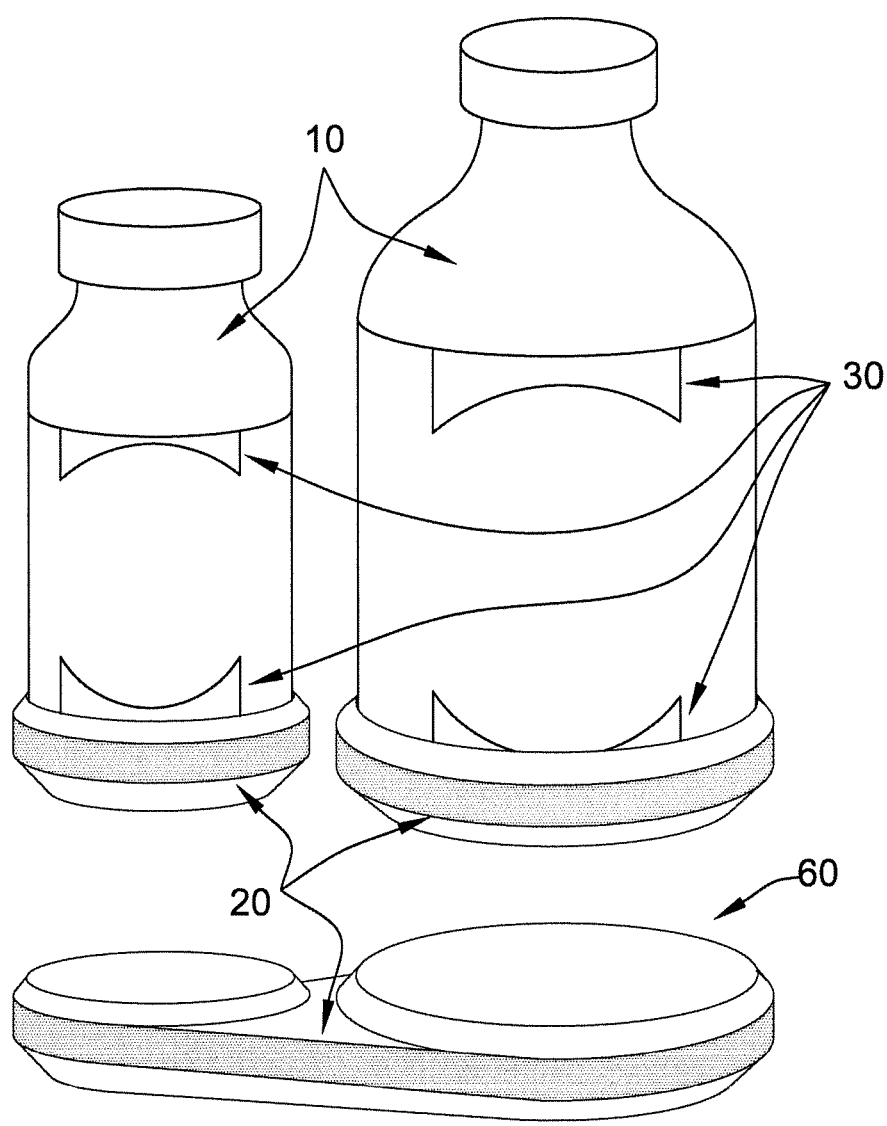
FIG. 12 shows an embodiment where the light member is a ring that fits around a pair of packages that comprise a medicament and includes an LED light source.

As shown in FIGS. 11 and 12, the light member 20 comprises an LED light source 50. In such an embodiment, the LED has at least an on/off switch (not shown) that can be activated by the end-user. In FIG. 11, the light member 20 is attached to the serum cap of the package 10 thereby providing an improved visual identification for the septa. In FIG. 12, the light member 20 is in the form of a band attached to the package 10 thereby providing improved visual identification in low light conditions. In this example, the light member is in the form of a band that fits around the bottom of a package. In another aspect, the light member is in the form of a tray or holder 60 where a two-part medicament is placed. In all aspects, the light member would not interfere with or affect the medicament inside the package during access by a syringe needle. In some aspects, the package would be suitable for use with an animal vaccination gun, and the light member would not interfere with loading the package into the vaccination gun. The light member may use any source of lighting as disclosed herein.

In the following, further features and aspects are described which can be realized in connection with any of the above-described embodiments and in any combination.

The package 10 according to the proposal is preferably for or comprises a medicament, in particular a vaccine. In particular, the package 10 is designed as a container for a liquid substance or a liquid vaccine, in particular as a bottle.

The emission of light by the light member 20 preferably is based on chemiluminescence. Thus, the emitted light is the result of a chemical reaction without need of electrical energy or external light or radiation acting on said light member 20. Accordingly, the light member emitting light based on chemiluminescence is particularly robust and reliable due to its autarkic operation.

The light member 20 is preferably configured to emit light for a predetermined period of time.

Preferably, the light member 20 is configured to emit light for several hours, for example for at least two hours, more preferably for at least four hours, in particular for at least six hours, most preferably for at least eight hours, and/or for at most 24 hours, more preferably for at most twenty hours, in particular for at most sixteen hours, most preferably for at most twelve hours.

The light member 20 preferably automatically stops emission of light after the predetermined period of time or is configured accordingly.

The period of time preferably complies with a minimum shelf-life of the content of the package 10, in particular when the package 10 has been unsealed or opened or starting with opening the package 10 and/or preparing the medicament/vaccine.

The chemicals preferably are configured and/or conditioned in a way such that said period of time is reached.

An activation of the light member 20 and/or the emission of light by the light member 20 is preferably induced by an active removing or destroying of a separator 140 between two different chemicals 120, 130, e.g., by a user of the package 10. Examples for such activation are described later with regard to FIGS. 13 to 16. Removing or destroying of the separator 140 preferably causes reaction of the chemicals 120, 130. Said reaction preferably causes or results in reaction of the chemicals 120, 130 causing emission of light by means of chemiluminescence. One or both of said chemicals preferably is/are liquid. This facilitates proper mixing.

Said activation can be triggered independently of opening of the package 10. Alternatively, or additionally, the period of time is (automatically) startable and/or (automatically) started when the package 10 is opened and/or when the medicament/vaccine is prepared.

Alternatively, or additionally, activation of the light member can be caused by exposing the light member 20 to light of a light source, in particular for a certain period of time such as at least two seconds or at least five seconds.

The package 10 which comprises the light member 20 or which is equipped with the light member 20 can be a secondary package or outer package. Thus, it is possible that the package 10 does not directly contain the medicament and/or that the package 10 is a package for a medicament which is contained in a further package such as a bottle. Such a secondary or outer package 10 is displayed in FIGS. 3, four, five, ten and twelve. A secondary or outer package 10 preferably is district of and/or separable from the further package 10 being in direct contract with a packaged substance like the medicament/vaccine. Alternatively, or additionally, the light member 20 is attached or fixed or configured to be attached or fixed directly to the package 10 directly containing the medicament/vaccine or the like. Thus, the term "package body" is used to encompass a container which directly contains the medicament/vaccine, as well as one or more containers and an outer packaging that at least partially encloses the one or more containers, or which joins a plurality of containers, each of which contains a medicament/vaccine and the container or containers. In contrast, the term "packaging material" is used to refer to the outer packaging by itself.

Preferably, the light member 20 emits light which is bright enough to enable a user to read written information on the package 10 or another package and/or to arrange for administration of a medicament/vaccine in a dark environment such as a barn. Preferably, the package 10 and/or light member 20 helps in reading information printed on the package such as information on the content of the package or operating instructions.

Preferably, the luminous flux of the light member 20 is at least 0.001 lm, more preferably at least 0.01 lm, in particular at least 0.1 lm, especially preferably at least 1 lm, most preferred at least 5 lm. Alternatively, or additionally, the light member 20 provides an illuminance of more than 0.1 lx, preferably more than 0.5 lx, in particular more than 1 lx or 2 lx. This preferably applies to an object illuminated by the light member, facing the light member 20 in a distance of 30 cm. Accordingly, the light member 20 preferably is configured for providing such luminous flux and/or illuminance.

Preferably, the light member 20 is arranged at the cap and/or the opening region of a bottle containing a medicament.

According to a particularly preferred aspect, the light member 20 is used for the packages 10 of medicaments or vaccines which are formed by mixing components before administration. Preferably, the light member 20 is activated upon opening of the packages 10 and/or upon mixing of the components, in particular wherein the predetermined period of time during which the light member 20 emits light corresponds to the stability or viability of the mixed components, i.e., the resulting medicament or vaccine, so that a user can easily infer whether or not the medicament or vaccine is still viable.

In the following, further features and aspects are described referring to very schematic sectional views of light members 20 as shown in FIGS. 13 to 18 which can be realized in connection with any of the above-described embodiments and in any combination, even if not explicitly mentioned. The same reference numerals are used for same or similar parts or parts of similar function, wherein the same or similar effects or advantages can be achieved even when not explicitly mentioned.

The light member 20 preferably comprises two cavities 100, 110 containing different (precursor) chemicals 120, 130 which, when coming into contact, cause chemiluminescent lighting. Alternatively, or additionally, fluorescent lighting can be caused this way. Said cavities 100, 110 preferably are closed off and separated from one another by separator 140.

A first of said chemicals 120, 130 preferably contains diphenyl oxalate while the other one contains hydrogen peroxide or vice versa. However, different chemicals 120. 130 can be used which are suited to cause light emission when being mixed.

Figure 13:
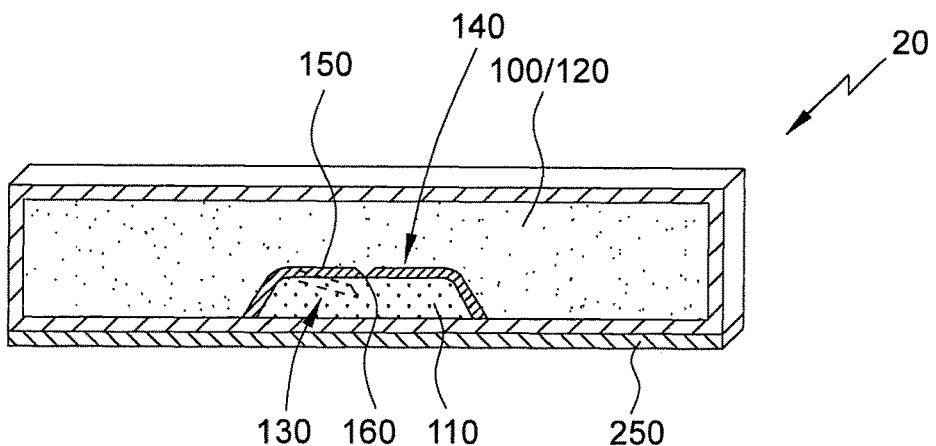
FIG. 13 is a schematic sectional view of one embodiment of the light member.

In a first embodiment as shown in FIG. 13, separator 140 preferably is a wall 150 separating said cavities 100, 110 from one another. The separator 140 preferably is frangible. Said separator 140 can comprise a predetermined breaking point 160, like a weak point, being configured to break more easily than the remainder of the separator 140. Said predetermined breaking point 160 preferably is configured to rupture when being manually pressed, causing the chemicals 120, 130 to mix, thus causing a reaction for emitting light.

Generally, the light member 20 preferably is configured to cause coming into contact and mixing up the chemicals 120, 130 of both cavities 100, 110 when the separator 140 is broken or ruptured or opened. Said separator 140 preferably is made of a brittle material or generally configured in a way such that it breaks under (manual) pressure/depression or bending, thus causing the chemicals 120, 130 to mix up and, preferably, chemiluminescence to start.

Figure 14:
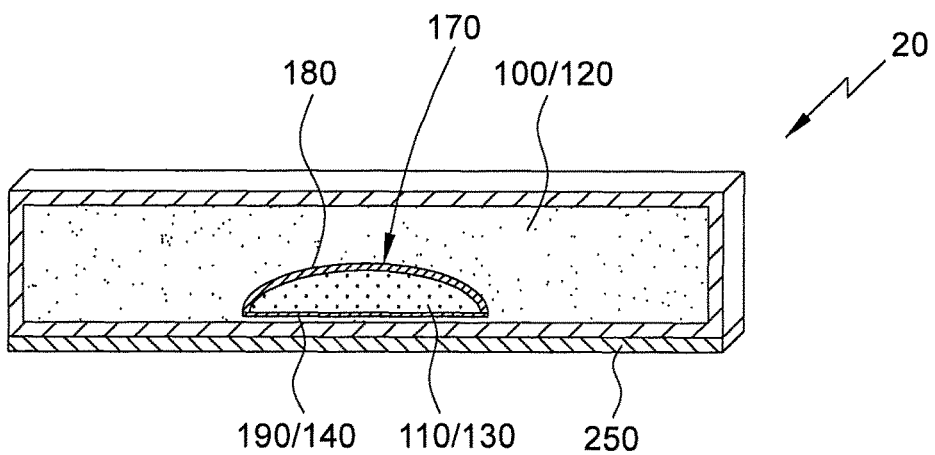
FIG. 14 is a schematic sectional view of another embodiment of the light member.

In a further embodiment shown in FIG. 14, one of said cavities 100, 110 forms a blister 170 or is realized as a blister 170.

A blister 170, also called blister package, is a cavity or pocket preferably made from a formable web 180, usually a thermoformed plastic. The blister 170 has a backing of a (lidding) seal 190, called blister film, e.g., of aluminum foil or plastic or a compound thereof. The blister 170 is configured that the web 180 forming the cavity or pocket is able to be dented, denting causing the content of the blister to act on the seal which, thus, breaks and releases the content.

In the present embodiment, one of said chemicals 120, 130 forms content of the blister 170. The seal 190 is the separator 140. Manually acting on the blister 170, thus, causes rupture of the seal 190 and the chemicals 120, 130 to come into contact. The blister 170 in the example shown in FIG. 13 forms the second cavity 110 and is arranged inside the first cavity 100. The latter, however, is not mandatory. In an alternative not shown, the seal 190 is arranged between the cavities 100, 110 while the blister web 180 is realized outside the first cavity 100.

Figure 15:
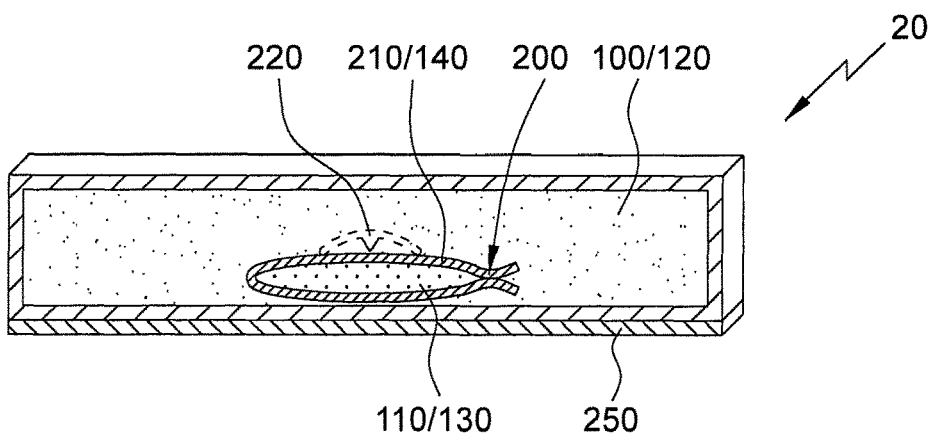
FIG. 15 is a schematic sectional view of another embodiment of the light member.

In a further embodiment shown in FIG. 15, the cavities 100, 110 are separated by means of a film valve 200 which is normally closed and automatically opens or is configured to be opened when pressure is applied to at least one of the cavities 80.

In particular, the second cavity 110 is a pouch 210 or capsule closed off by said film valve 200 which opens and releases its chemical 130 when acting on it, in particular pressing it, which causes the film valve 200 to—preferably irretrievably—open.

The film valve 200 can be formed by wall sections of the second cavity 110 which are attached—preferably separably glued, separably welded or separably adhered to one another such that a fluid barrier is caused and which can be separated from one another such that a fluid passage is established between said cavities 100, 110.

Particularly preferably, the film valve 200 is formed by a weld seam being frangible such that the weld seam can be manually broken. In particular, the weld seam merely causes a temporal adhesion. However, different film valves 200 being closed by temporal adhesion and openable by overcoming this temporal adhesion can be used as well.

Alternatively or additionally, the separator 140 comprises a piercing element 210 which is configured to pierce the separator 140. An example for said piercing element is depicted using dashed lines in FIG. 15. Manually depressing said piercing element 220 breaks the separator 140 causing the chemicals 120, 130 to come into contact (and to react).

Figure 16:
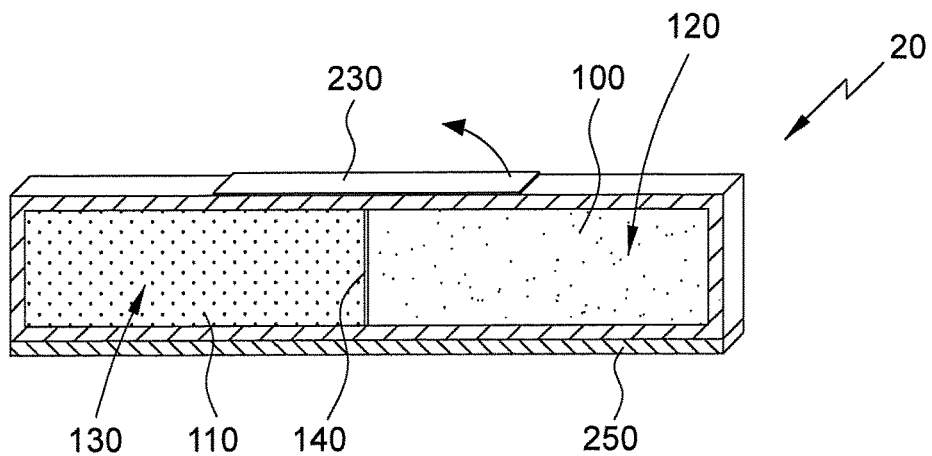
FIG. 16 is a schematic sectional view of another embodiment of the light member.
Figure 17:
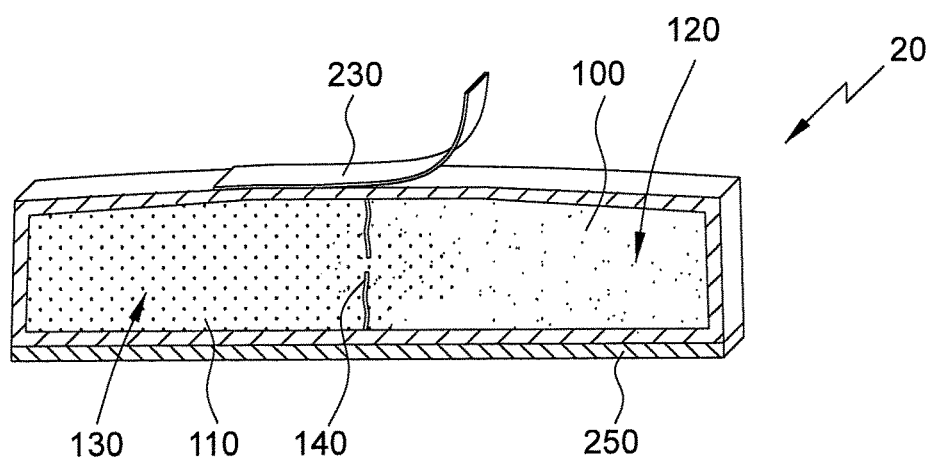
FIG. 17 is a schematic sectional view of the light member of FIG. 16 in activated state.

In one further embodiment depicted in FIGS. 16 and 17, the cavities 100, 110 are formed by a compartment forming at least essentially the lighted number 20 and being divided by a separator 140 formed by a frangible film extending across said compartment. The compartment/light member 20 is configured to be bulged causing the separator 140 to be stretched such that the separator 140 ruptures. In the example shown, a tab 230 is arranged at the compartment enabling the compartment to be bulged such that the separator 140 ruptures. In particular, the tab 230 is a peel-off tab being adhered to the compartment with an adhesive force such that removing the peel-off tab ruptures the separator 140.

Generally speaking, the chemical reaction of the chemicals 120, 130 can be started or startable by tearing and/or removing a pull tab from the lighting member 20, either as described referring to FIGS. 16 and 17, or in a different manner.

Figure 18:
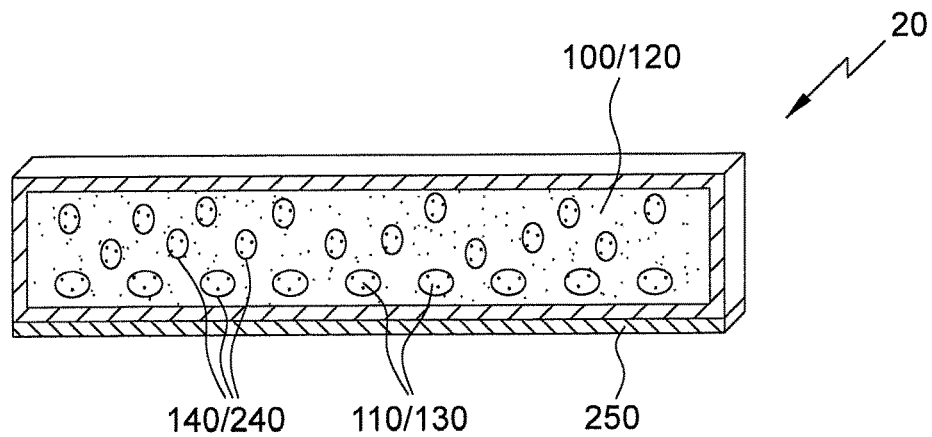
FIG. 18 is a schematic sectional view of another embodiment of the light member.

In a further embodiment as depicted schematically for example in FIG. 18, the chemicals 120, 130 are separated from one another by means of one or more frangible capsules 240 or microcapsules containing one of the chemicals 120, 130 and, thus, separating it from the other one of the chemicals 120, 130.

Breaking one or multiple of said capsules 240 or microcapsules then causes mixing up and reaction of the chemicals 120, 130 causing the light member 20 to emit light, preferably based on chemiluminescence.

The capsules 240 or microcapsules can form separators 140 as they enclose one of the chemicals 120, 130. Thus, the capsules 240 or microcapsules separate the chemicals 120, 130 from one another by means of frangible walls which can be formed by or comprise one or more or combinations of: lipids, phospholipids, waxes, resins like shellac, epoxide, polysaccharide, protein like casein, polymer like polyamide, polyacrylate, polyethylengylcole and polyurethane or enorganic materials like silicon oxide, titan oxide or ferric oxide.

The capsules 240 or microcapsules preferably have an average or minimum diameter of less than 2 mm or 1 mm, preferably less than 500 μm, less than 100 μm or less than 50 μm; and/or more than 5 μm, preferably more than 10 μm, in particular more than 20 μm.

The capsules 240 or microcapsules containing one of the chemicals 120, 130 can be arranged within, in particular be suspended in the other one of the—preferably liquid—chemicals 120, 130 such that destroying, e.g., by breaking the wall of the said capsules 240 or microcapsules causes the light member 20 to emit light, preferably by chemiluminescence.

Alternatively, or additionally, the capsules 240 or microcapsules forming second cavities 110 containing the second chemical 130 can be immobilized within the first cavity 100 containing the other, first chemical 120. This is also shown in FIG. 18 as the undermost capsules 240 or microcapsules are adhered or fixed at a (bottom) wall inside the first cavity 100. This provides the advantage that the capsules 240 or microcapsules might be easier to destroy on manual depressing the light member 20.

Alternatively, or additionally, a different kind of mechanism can be provided, which preferably opens the separator 140, causing or enabling mixing up the chemicals 120, 130 and causing the light member 20 start emitting light on manually acting thereon. Further, the mechanisms as described can be realized independently and in combination.

In one alternative, the first chemical 120 of the chemicals 120, 130 causing the light member 20 to emit light can be stored in at least one glass capsule 240 or closed glass tube forming the separator 140 and having a wall thickness allowing to be broken by depression or bending, in particular less than 0.2 or 0.1 mm. Alternatively or additionally, said capsule 240 is a second cavity 110 closed off by a frangible flexible and/or frangible elastic film.

Generally speaking, the light member 20 in some examples has a separator 140 which is configured to be ruptured by manually pressing the light member 20 by means of a user's thumb or by manually bending the light member 20, by at least 15° and/or less than 45° and/or by bending it.

Preferably, the light member 20 can be activated (the separator 140 can be ruptured or made permeable otherwise) by attaching the light member 20 to a bottle wall having a radius of less than 10 cm and/or more than 2 cm. In particular, the light member 20 is activatable by bending with a radius of less than 15 cm or 10 cm.

The light member 20 preferably forms a patch and/or has an adhesive layer 250 for being attached to or held on a package 10 like a bottle. This adhesive layer 250 can be arranged on an outer surface/flat face of the first cavity 100 like depicted in the examples of FIGS. 13 to 18. The light member 20 can be fixed to the package 10 by means of the adhesive layer 250 or can be arranged for being fixed. For this purpose, the adhesive layer 250 might be covered by a pull tab (not shown) which can be removed to uncover the adhesive layer 250 in order to enable fixing the light member 20 to a package 10 afterwards. However, no or different means for fixing or holding the light member 20 can be provided alternatively or additionally.

Different aspects of the present invention can be realized separately and in different combinations.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A package comprising:
   a package body comprising at least one container,
   a medicament in the package body, and
   a light member,
   wherein the light member is located on the exterior of the package body, and
   wherein the light member is configured to provide information to an end user by the emission of light,
   wherein the information provided to the end user is related to the viability of the medicament,
   wherein the light member is configured to emit light for a predetermined period of time, and
   wherein the light emission is produced by chemiluminescence and the light member is adapted to be activated upon active opening of the package body.

2. The package according to claim 1, wherein the medicament is a veterinary product selected from the group consisting of antibiotics, vaccines, nutritional supplements, growth supplements, antifungal medication, antiparasitic medication, hormones or combinations thereof.

3. The package according to claim 1, wherein the medicament is a vaccine for bovine viral diarrhea.

4. The package according to claim 1, wherein the light member comprises part of a label on the package body.

5. The package according to claim 1, wherein the light member is actuatable by a combination of two or more chemicals.

6. The package according to claim 5, wherein the chemicals are kept separate by a separator inside the light member.

7. The package according to claim 6, wherein the separator is ruptured for mixing the chemicals by exerting force on the separator.

8. A method for determining the viability of a medicament in a package, said method comprising:
   activating a chemiluminescent light member on a package body comprising at least one container containing a medicament upon active opening of the package body; and
   observing the chemiluminescence in the light member, wherein the light member fluoresces or emits chemiluminescent light for a period of time equal to a length of time for which the medicament remains viable.

9. The method according to claim 8, wherein said activating of the light member comprises causing two or more precursor chemicals to mix.

10. The method according to claim 8, wherein said activating of the light member comprises exposing the light member to light for at least a set time period based on the shelf life of the medicament.

11. The method according to claim 8, wherein the medicament is a veterinary product selected from the group consisting of antibiotics, vaccines, nutritional supplements, growth supplements, antifungal medication, antiparasitic medication, hormones and combinations thereof.

12. The method according to claim 8, wherein the medicament is a vaccine for bovine viral diarrhea.

13. The method according to claim 8, wherein said activating comprises rupturing a separator which keeps two or more precursor chemicals separate.

* * * * *